United States Patent
Johns et al.

(10) Patent No.: US 9,007,220 B2
(45) Date of Patent: Apr. 14, 2015

(54) ALERTNESS SENSING DEVICE

(75) Inventors: Murray Johns, Richmond (AU);
Christopher Hocking, Richmond (AU)

(73) Assignee: Optalert Pty Ltd, Richmond (AU)

( * ) Notice: Subject to any disclaimer, the term of this patent is extended or adjusted under 35 U.S.C. 154(b) by 643 days.

(21) Appl. No.: 13/054,020

(22) PCT Filed: Jul. 17, 2009

(86) PCT No.: PCT/AU2009/000908
§ 371 (c)(1),
(2), (4) Date: Jan. 13, 2011

(87) PCT Pub. No.: WO2010/006370
PCT Pub. Date: Jan. 21, 2010

(65) Prior Publication Data
US 2011/0121976 A1    May 26, 2011

(30) Foreign Application Priority Data
Jul. 18, 2008    (AU) ................................. 2008903660

(51) Int. Cl.
| | | |
|---|---|---|
| G08B 17/12 | (2006.01) | |
| G08B 21/06 | (2006.01) | |
| A61B 3/113 | (2006.01) | |
| A61B 5/11 | (2006.01) | |
| A61B 5/00 | (2006.01) | |
| B60K 28/06 | (2006.01) | |

(52) U.S. Cl.
CPC .............. *G08B 21/06* (2013.01); *A61B 3/113* (2013.01); *A61B 5/1103* (2013.01);
(Continued)

(58) Field of Classification Search
CPC .......... A61B 3/113; A61B 5/11; G06F 3/013; G06F 3/011; G02B 27/017; G02B 2027/0187; G02B 2027/0178
USPC ................................. 340/500, 540, 573.1, 576
See application file for complete search history.

(56) References Cited

U.S. PATENT DOCUMENTS

| 3,999,177 A | 12/1976 | Greene |
|---|---|---|
| 5,745,038 A | 4/1998 | Vance |

(Continued)

FOREIGN PATENT DOCUMENTS

| AU | 699793 B2 | 12/1998 |
|---|---|---|
| WO | WO-0225615 A1 | 3/2002 |

(Continued)

*Primary Examiner* — James Yang
(74) *Attorney, Agent, or Firm* — Novak Druce Connolly Bove + Quigg LLP

(57) ABSTRACT

A head worn device for monitoring alertness and attention which includes a) sensors to monitor eyelid and eye movement, b) a motion sensor and c) data storage means for storing data from said sensors. The motion sensor is an accelerometer to provide data that allows the head position to be analyzed and to determine the direction of gaze. The device collects data from an accelerometer worn by the driver to detect if the vehicle is in motion and whether the head is tilted vertical plane. If the vehicle is not in motion data is not processed. When the direction of gaze is downward sensor signals from the eye movement sensors is ignored. However if the duration of downward gaze is greater than a predetermined minimum period and the vehicle is in motion, an alarm is triggered because the driver is inattentive. The device may be used to assess whether workers are sufficiently alert before they commence work. The method of measuring a subjects fitness for a particular task uses the alertness monitor or a video camera to monitor eye and eyelid movement with or without head movement data while the subject is tested with a series of tests that require the subject to follow predetermined images or lights. If the subject is unable to satisfactorily track the images the subject is not fit for work.

3 Claims, 8 Drawing Sheets

(52) U.S. Cl.
CPC ...... *A61B 5/6814* (2013.01); *A61B 2562/0219* (2013.01); *B60K 28/06* (2013.01); *A61B 5/6803* (2013.01); *A61B 5/6821* (2013.01); *A61B 2503/22* (2013.01)

(56) References Cited

U.S. PATENT DOCUMENTS

| | | | |
|---|---|---|---|
| 6,107,922 | A | 8/2000 | Bryuzgin |
| 6,147,612 | A | 11/2000 | Ruan et al. |
| 6,154,141 | A | 11/2000 | Prater et al. |
| 6,927,694 | B1 | 8/2005 | Smith et al. |
| 7,027,621 | B1 * | 4/2006 | Prokoski ..................... 382/118 |
| 2001/0028309 | A1 | 10/2001 | Torch |
| 2003/0088906 | A1 * | 5/2003 | Baker .............................. 2/416 |
| 2003/0144088 | A1 * | 7/2003 | Shoane ........................ 473/405 |
| 2005/0007552 | A1 | 1/2005 | Fergason et al. |
| 2005/0196009 | A1 * | 9/2005 | Boesen ........................ 381/380 |

FOREIGN PATENT DOCUMENTS

| | | |
|---|---|---|
| WO | WO-2005094667 | 10/2005 |
| WO | WO 2007016739 A1 * | 2/2007 |
| WO | WO-2007016739 A1 | 2/2007 |

\* cited by examiner

ALERTNESS SENSING DEVICE

CROSS REFERENCE TO RELATED APPLICATIONS

This application is a National Phase filing under 35 U.S.C. §371 of PCT/AU2009/000908 filed on Jul. 17, 2009; and this application claims priority to Application No. 2008903660 filed in Australia on Jul. 18, 2008 under 35 U.S.C. §119; the entire contents of all are hereby incorporated by reference.

This invention relates to improvements in devices used in monitoring eye and eyelid movement and is concerned with monitoring alertness and inattention particularly in vehicle and machinery operators.

BACKGROUND TO THE INVENTION

The detection of drowsiness is of importance because drowsiness impairs the ability of operators of a wide range of equipment including motor vehicles, aircraft and boats as well as industrial equipment WO 03/039358 disclosed an alertness monitor that used infra red light to measure the amplitude and velocity of eyelid and eye movements to derive a measure of Drowsiness on a scale. This monitor sought to provide a real time alertness monitor that can provide a calibrated measure of the operator's alertness.

WO 2007/016739 discloses spectacles for use in the eye monitoring system of WO 03/039358, which include a pair of ocular frames and a sensor unit adapted to be positioned adjacent an eye of the wearer. A nose bridge connects the ocular frames and incorporates an adjustment mechanism for adjusting the vertical position of the sensor unit relative to the eye. A frame arm extends from the outer edge of each ocular frame and is adapted to fit over the ear of a wearer. The sensor unit incorporates two infra red emitters at different angles and an infra red detector recessed into the surface of the unit to reduce the proportion of signal received by said detector which is not from the signal emitter reflected by the eye or eyelids. There is a recent concern with the problem of driver inattention and distraction, not just drowsiness. By distraction they mean displacement of the driver's focus of visual attention from the driving task, either to a non-visual task (eg talking to other people in the vehicle, or the use of mobile phones), or to an alternative, visual task that reduces driving safety temporarily (reading a map or navigation system, adjusting a CD player or radio, etc). Thus, driver distraction is concerned with attention that is focused inappropriately, in direction and duration, for safe driving. There has been a number of attempts to deal with inattention by drivers.

EP 168788 discloses a method of monitoring inattentiveness by monitoring the steering of the vehicle.

USA patent application 2005/0030184 discloses a vehicle control subsystem that senses a level of the drivers attention compared to the current state of the vehicle.

USA patent application 2007/0008151 discloses a method of detecting drowsiness and or inattention by analysing head movements or head movement reactions of the driver.

U.S. Pat. No. 7,344,251 discloses a method of determining mental alertness by monitoring the subjects point of gaze and pupillary movements and pupillary response in performing a task, analysing the responses and calculating an alertness score.

It is an object of this invention to provide an improved method of monitoring overall alertness including drowsiness and inattention.

BRIEF DESCRIPTION OF THE INVENTION

To this end the present invention provides a head worn device for monitoring alertness and attention which includes
a) sensors to monitor eyelid and eye movement
b) a motion sensor and
c) data storage means for storing data from said sensors.

Preferably the motion sensor is an accelerometer more preferably a 3 dimensional accelerometer. The accelerometer can provide data that allows the head position to be analysed and to assist in assessing the direction of gaze. The sampling frequency is not critical but 100 Hz is preferred. By combining information relating to head movement and eye movement information relating to attention and alertness can be combined.

The system will include at least one micro processor to process the signals from the eye sensors and the 3 dimensions of the accelerometer. This processor may be included in the head worn device or in a separate unit to which the sensor signals are sent. The processors may be of the type disclosed in WO 03/039358.

In a preferred embodiment the spectacle sensor disclosed in WO2007/016739 is modified to include a 3 dimensional accelerometer in an arm of the spectacle frame. Although accelerometers have been used in head worn devices these have not been for the purpose of determining alertness or inattention.

U.S. Pat. No. 6,730,047 discloses the use of motion sensors on head wear to detect the position and inclination of the head for use in analysing sports performance.

USA application 2007/0161875 discloses head gear for use in diagnosing vestibular disorders. The head gear includes motion sensors and stimuli deliverers.

Patent application WO 2007/088374 discloses a device incorporating accelerometers mounted near the ear for use in gait analysis.

Patent application 2008/020362 discloses body worn motion sensors to assist visually handicapped persons.

Although the eye and eyelid movements collected by the device of this invention, may indicate that the subject is alert, head position may indicate that the subject is not looking in the appropriate direction or that the amount of time spent looking in a particular direction is too long. For example when driving looking at the mirrors or instruments is appropriate but too long can be distracting the drivers attention from what is happening in the direction of travel.

In another aspect of this invention there is provided in an alertness and attention monitor for vehicle drivers which collects data from an accelerometer worn by the driver to detect if the vehicle is in motion and whether the head is tilted vertical plane. If the vehicle is not in motion alertness and attention data are not displayed. When the direction of gaze is downward sensor signals from the eye movement sensors may be ignored if other variables do not indicate drowsiness. However if the duration of downward gaze is greater than a predetermined minimum period and the vehicle is in motion, an alarm is triggered because the driver is inattentive. The alertness monitor of this invention is primarily used for determining whether a driver or operator is growing tired or inattentive while actually driving. However there is a need to be able to assess whether workers are sufficiently alert before they commence work. To this end the present invention provides a method of measuring a subjects fitness for a particular task by using an alertness monitor of this invention or that described in patent WO 03/039358 or WO 2007/016739 or alternatively a video camera to monitor eye and eyelid movement with or without head movement data while the subject is tested with a series of tests that require the subject to follow predetermined images or lights. If the subject is unable to satisfactorily track the images the subject is not fit for work.

DETAILED DESCRIPTION OF THE INVENTION

A preferred embodiment of the invention is illustrated in the drawings in which.

Figure 5A:
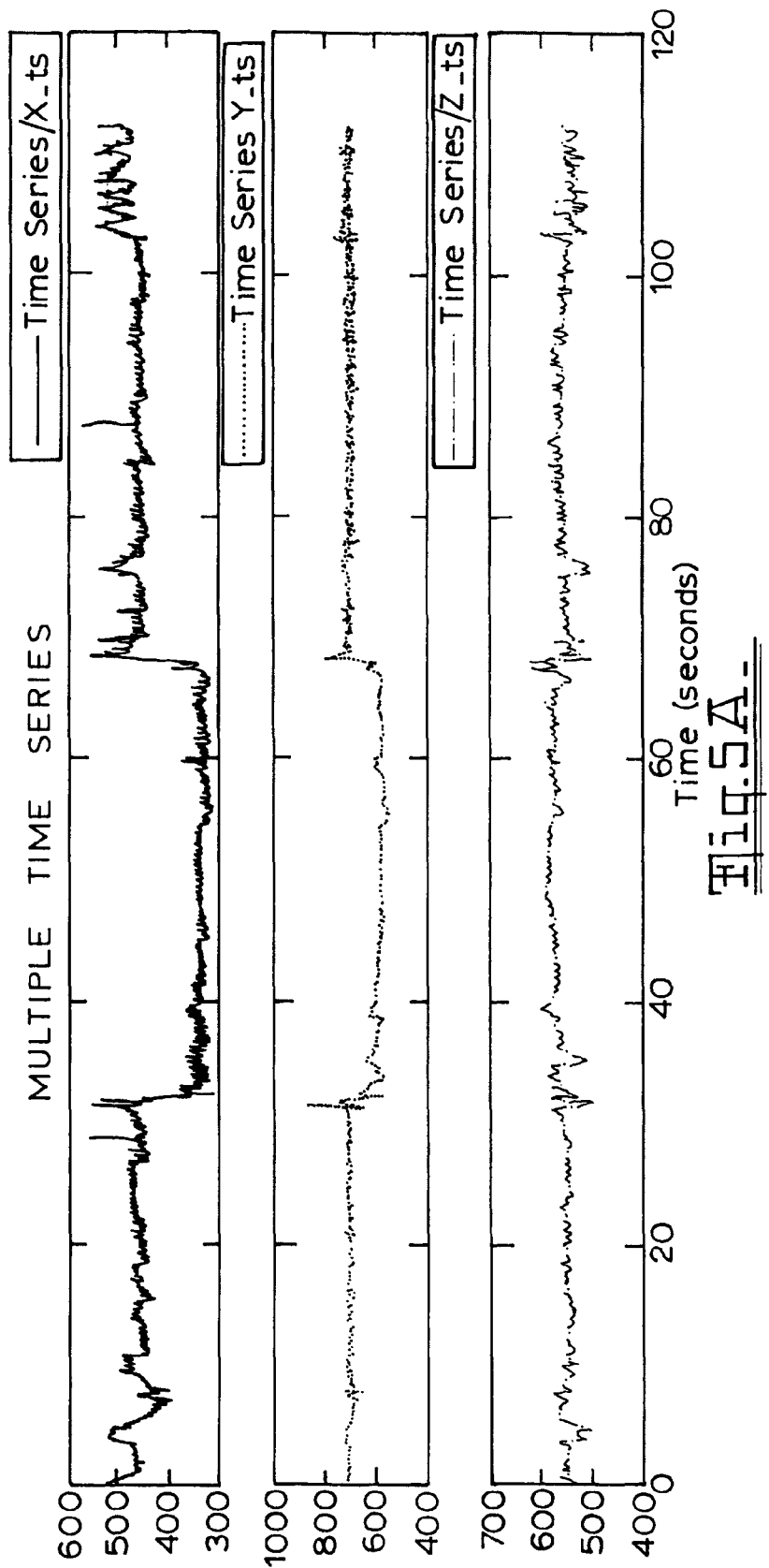
Figure 5B:
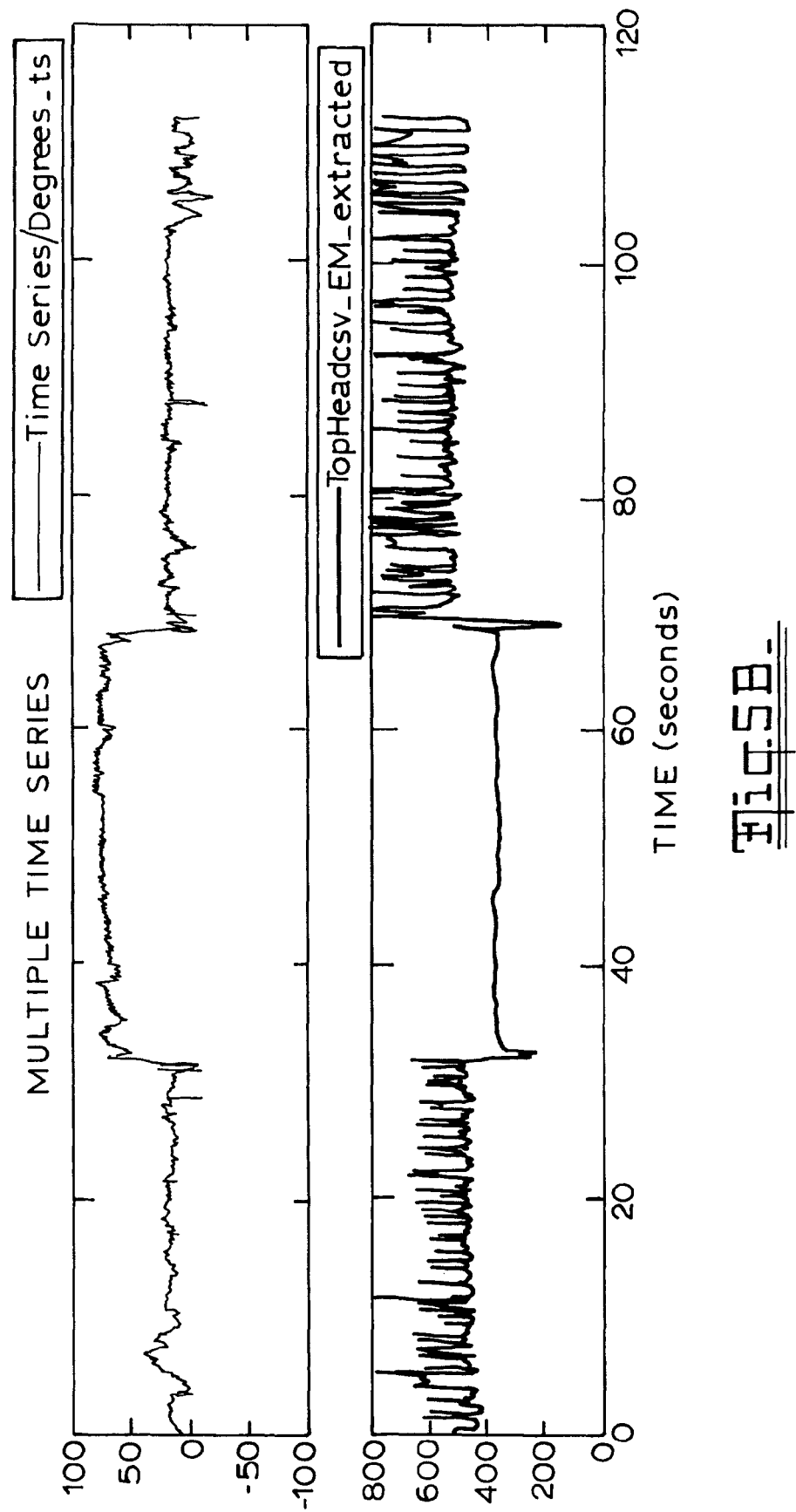
Figure 5A:
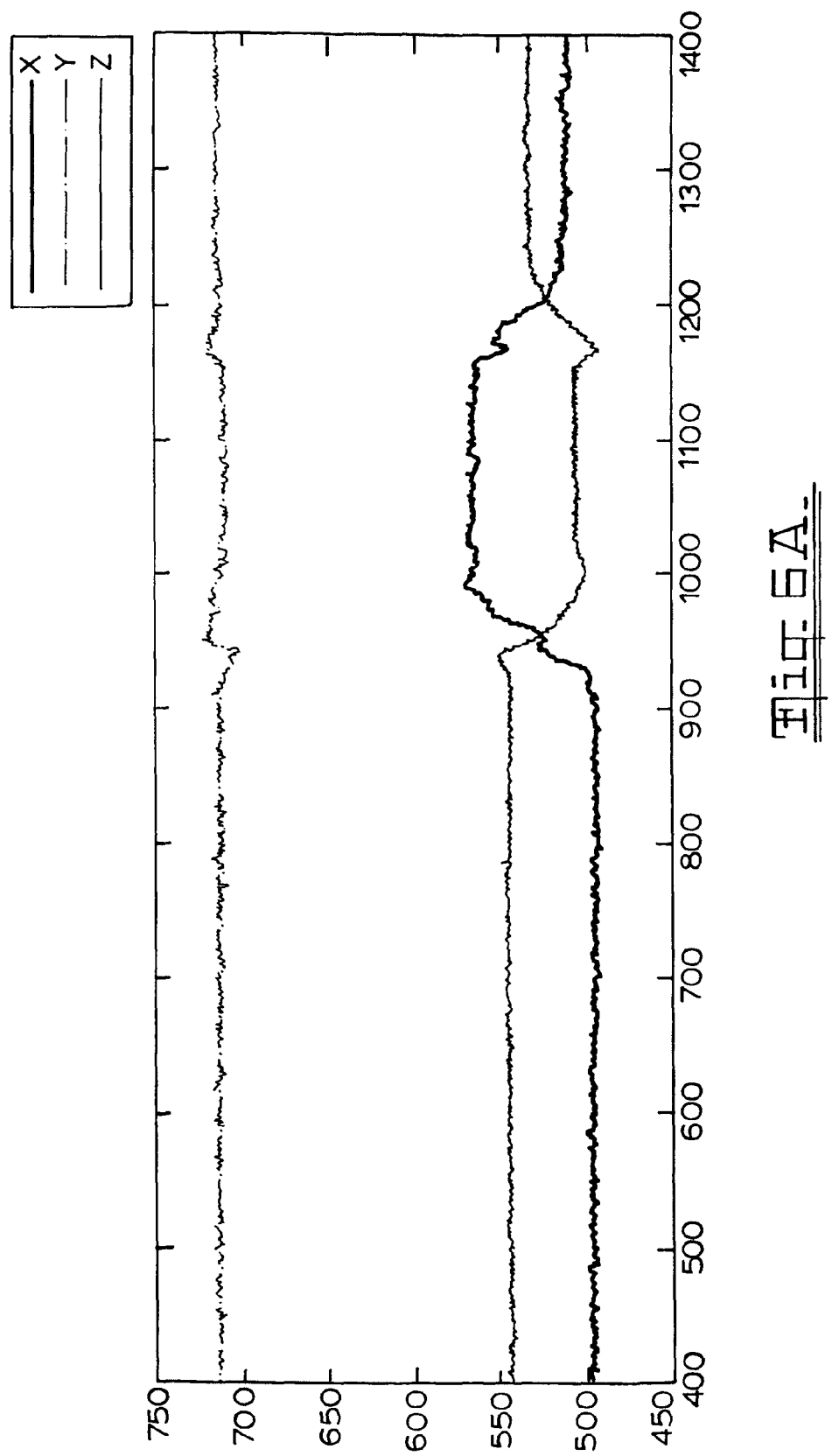
Figure 6B:
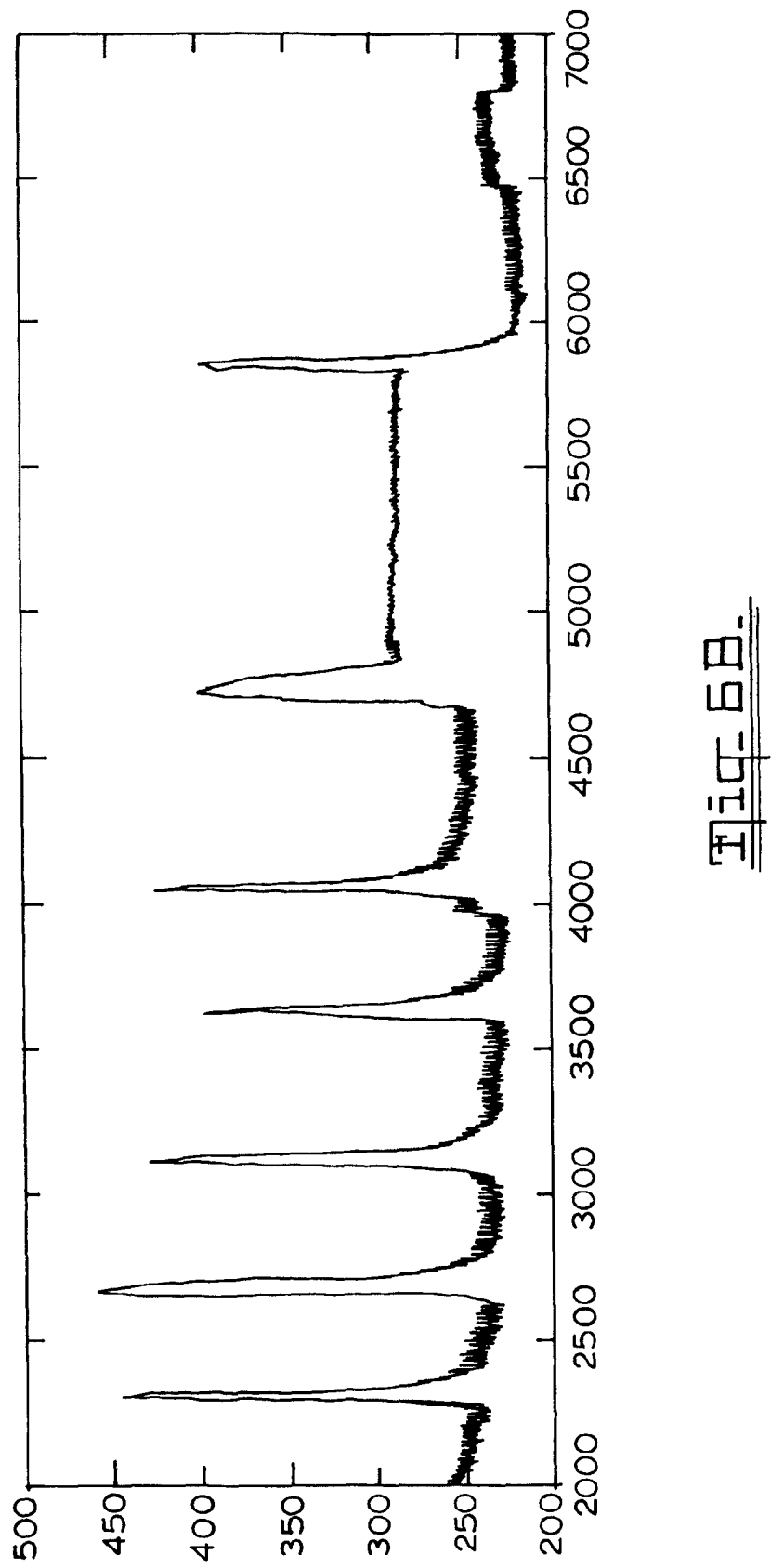

FIG. 5 A shows the 3 axes of accelerometer data when a driver places the glasses on the top of his head;

FIG. 5B shows the derived tilt data (top) from the accelerometer readings of FIG. 5A and the corresponding eye movement data (bottom);

FIG. 6A illustrates the signals from the 3 accelerometer axes and FIG. 6 B the corresponding eye movements when the head is stationary for 5 blinks followed by two blinks during a head movement looking down and to the left.

Due to the fixed position of the glasses on the wearers head, the accelerometer gives an indication of head position in relation to that when looking straight ahead (e.g., at the road ahead when driving).

The glasses contain a 3-axis digital accelerometer located in the left arm of the glasses. A separate digital output from each axis (X, Y & Z) is given. These outputs can be used individually, or a combination of two axes can be used to give an indication of movement in three planes (tilt, roll and yaw).

Figure 1:
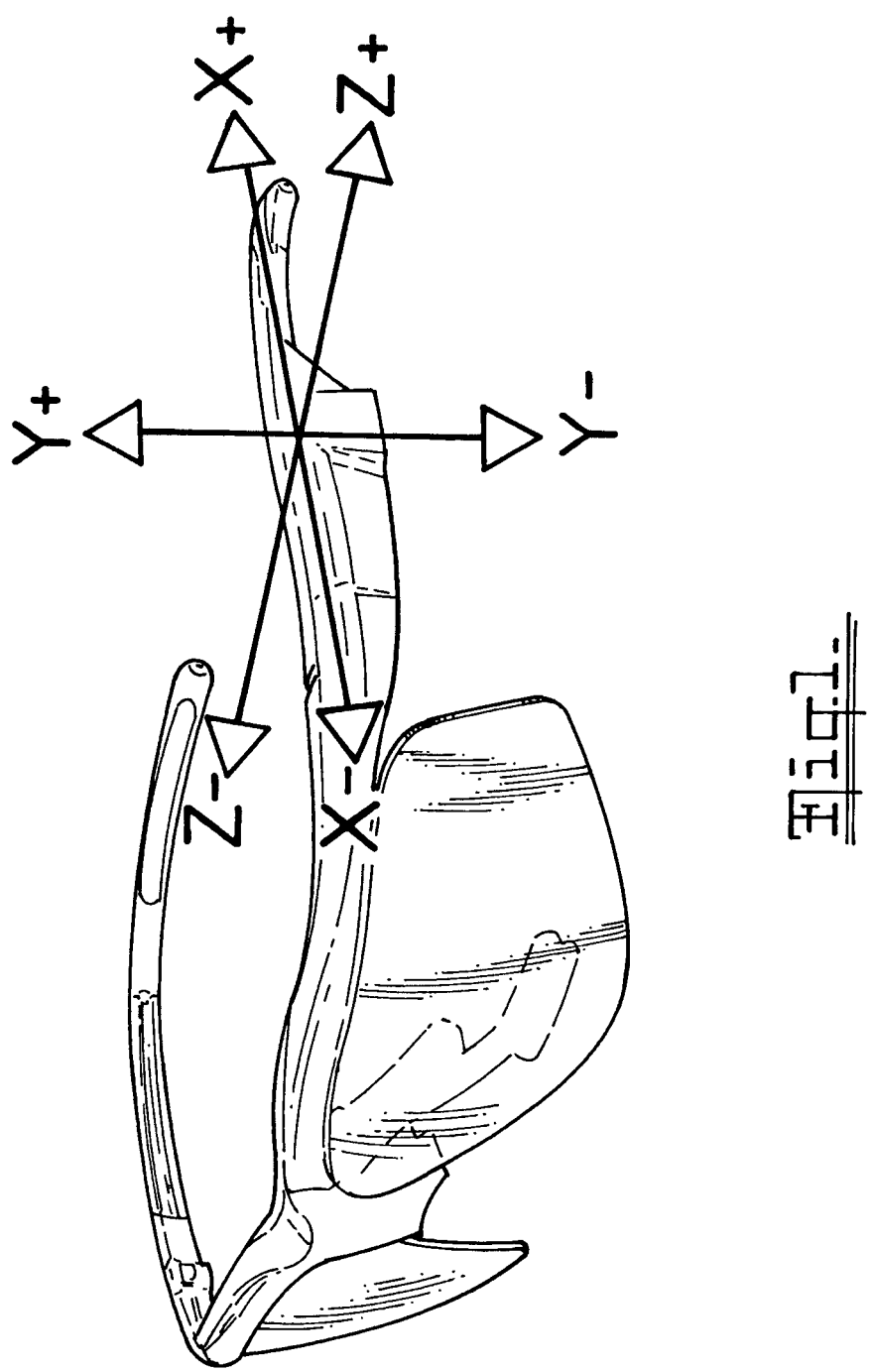
FIG. 1 illustrates a spectacle monitor of this invention.

Output from the accelerometer is sampled at a rate of 100 Hz (but lower sampling rates are suitable if the information content of the signal is not adversely impacted) and preferably digitized at 10 bit resolution or higher. The chosen accelerometer has a range of ±2.5 g, and therefore a resolution of 0.00488 g FIG. 1 shows the orientation of the accelerometer axes when mounted in glasses of the kind disclosed in WO 2007/016.

The spectacle frame will incorporate a PCB on which the accelerometer and the microprocessor are mounted. A preferred accelerometer is a Kionox Kx[pS5-2050+/−2 g Tri Axis accelerometer.

Movement in Three Planes

Tilt

Refers to movement in the XY plane. This would correspond to the glasses wearer facing directly ahead, but looking either up (inclination) or down (declination).

Figure 3:
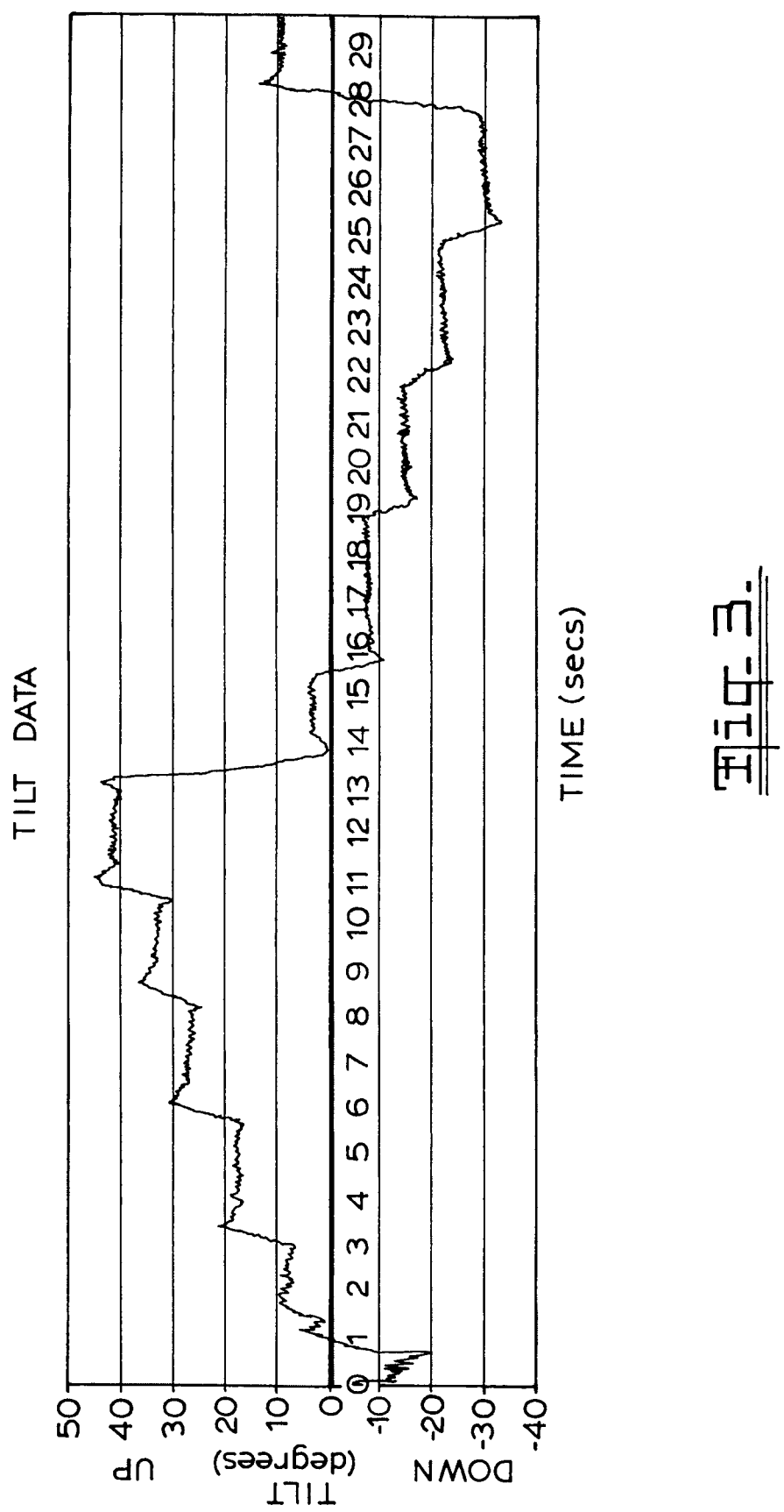
FIG. 3 illustrates the signals in the vertical plane of a series of head movements upwards and then downwards.

Application:

Tilt can be used to indicate whether a wearer is maintaining their view of the road ahead (assumed to be indicated by roughly horizontal attitude of the glasses and a near-zero tilt reading) or whether they are looking away from the road at objects within the vehicle interior (radio, gearstick etc). See FIG. 3.

Method:

Tilt can be measured by taking the x-axis output and the y-axis output, and applying a trigonometric function to obtain the angle of tilt (declination or inclination). The x-axis must be translated negatively in order to yield a positive value for inclination and a negative value for declination.

$$\arctan\left(\frac{-x}{y}\right) = \text{angle}(rads)$$

Conversion into degrees of angle can be obtained by multiplying the above result by 180/pi.

Further filtering of the Degrees signal is used to remove high frequency components and provide a 'cleaner' signal for a software state machine to categorise the head tilts.

Roll

Refers to movement in the YZ plane. This corresponds to the glasses wearer rolling their head to the left or right side (bringing the ear closer to the shoulder).

Theoretically, we could measure the angle of head roll similarly to head tilt, but this would be unlikely to yield any useful information (this is an atypical head position and would likely have little relevance to the operation of the alertness monitoring system).

Yaw

Refers to movement in the XZ plane. This corresponds to the glasses wearer turning their head left or right.

Figure 4:
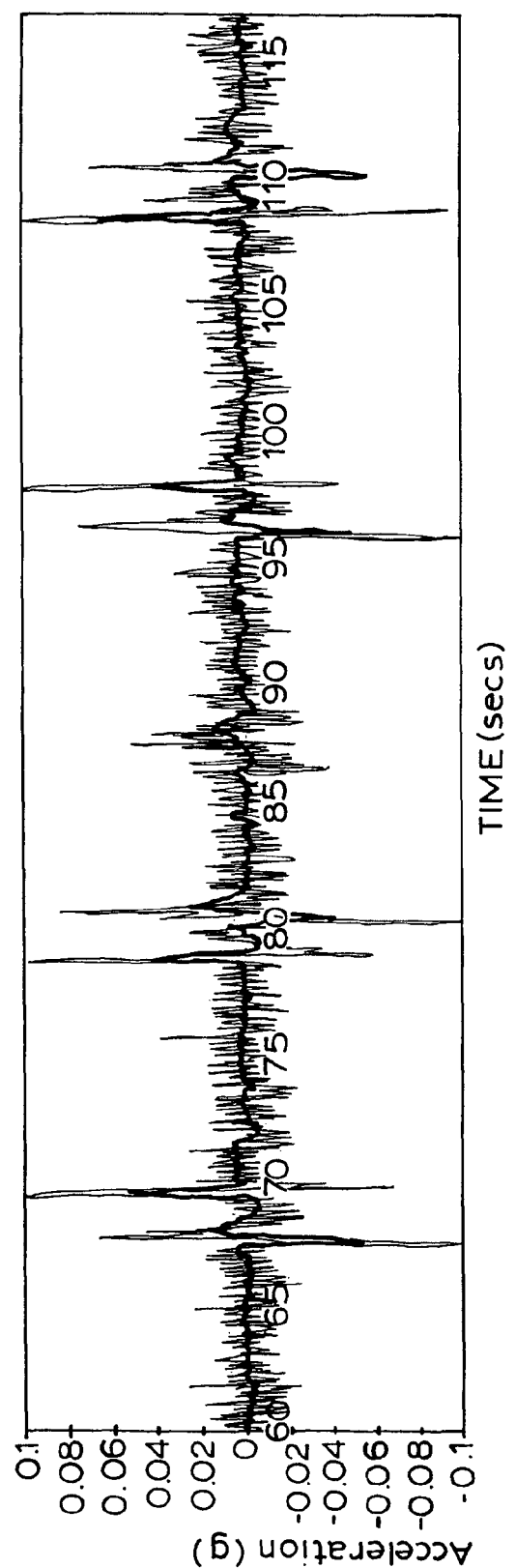
FIG. 4 illustrates the signals in the horizontal plane of a series of head turns, left, right, left, right.

See FIG. 4.

Application:

Detection of horizontal head movements could form the basis for an "inattention" warning, which would be given if a wearer's head was directed away from the straight ahead position for longer than a given period of time.

Methodological Issues:

Large accelerations in lateral directions can be detected by the accelerometer X & Z axes. However, quantifying the head position (how far the head has turned) from accelerations alone is almost impossible, since a slow head turn of 90 will show low accelerations and a quick 90 head turn will show high accelerations. This data will not indicate the final head position accurately, because of inaccuracies introduced by the double integration needed to go from acceleration to velocity, and then to position.

Unlike the XY plane, which can track vertical movements and where gravity acts as a constant acceleration in one direction, thereby giving consistent values for given head positions, it is extremely difficult to track horizontal head position given the tendency for the zero-degree (straight-ahead) point to "wander". That is, a head turn to the left may be followed by a corrective head turn to the right (to restore the straight-ahead position), but the magnitude of these turns (accelerations) may be different, leading to the straight-ahead position registering a different value than originally.

However, the direction in which the head is turned can be interpreted from the acceleration data using the differential response of the X and Z axes to left and right head turns.

Compound Movements

Natural head movements will more commonly be compound or multi-axis movements (ie., looking down and to the left), but the X, Y & Z components of such movement will be detectable in each corresponding axis.

FIGS. 6 A and 6B illustrate a combined set of signals when the head is stationary for 5 blinks followed by two blinks during a head movement looking down and to the left.

FIGS. 5 A and 5B illustrate the signals which can indicate when the glasses have been taken off.

Derived Measurements

Other useful information can be derived by applying various signal processing techniques to the data output from each axis of the accelerometer. See FIGS. 2 and 5B.

Vehicle Motion
Detection of Vehicle Motion
Application:

Danger to the driver or others is typically limited to when the vehicle is in motion. A driver sitting in a stationary vehicle may receive inappropriate warnings from the Optalert system in some situations (closing eyes at traffic lights, filling in logbooks etc). By detecting vehicle motion, the system may be "paused" to prevent these inappropriate warnings. See FIG. 2.

Method:

By looking at the output from the Y-axis of the accelerometer, we can get an indication of the movement of the accelerometer in the vertical axis caused by the movement of the vehicle on the road.

Experimental data indicates that a reliable method of detection of vehicle motion states (In Motion or Stationary) is possible by applying some signal processing to this Y-axis data output.

The Y-axis will consistently output a signal equivalent to approximately 1 g of force when the Y-axis is parallel to the direction of gravity. On top of this signal, vibratory movement due to the movement of the car along the road will be superimposed, leading to a fluctuation in the Y-axis signal. This vibratory movement in the y-axis has been shown to diminish significantly when the vehicle is at rest, leading to a reduction in the fluctuation of the y-axis data.

Analysing the data in a statistical manner indicates that when the vehicle is moving, the variance (amount of fluctuation) in the signal is significantly higher than when the vehicle is at rest (fluctuation about the 1 g level is minimal).

Figure 2:
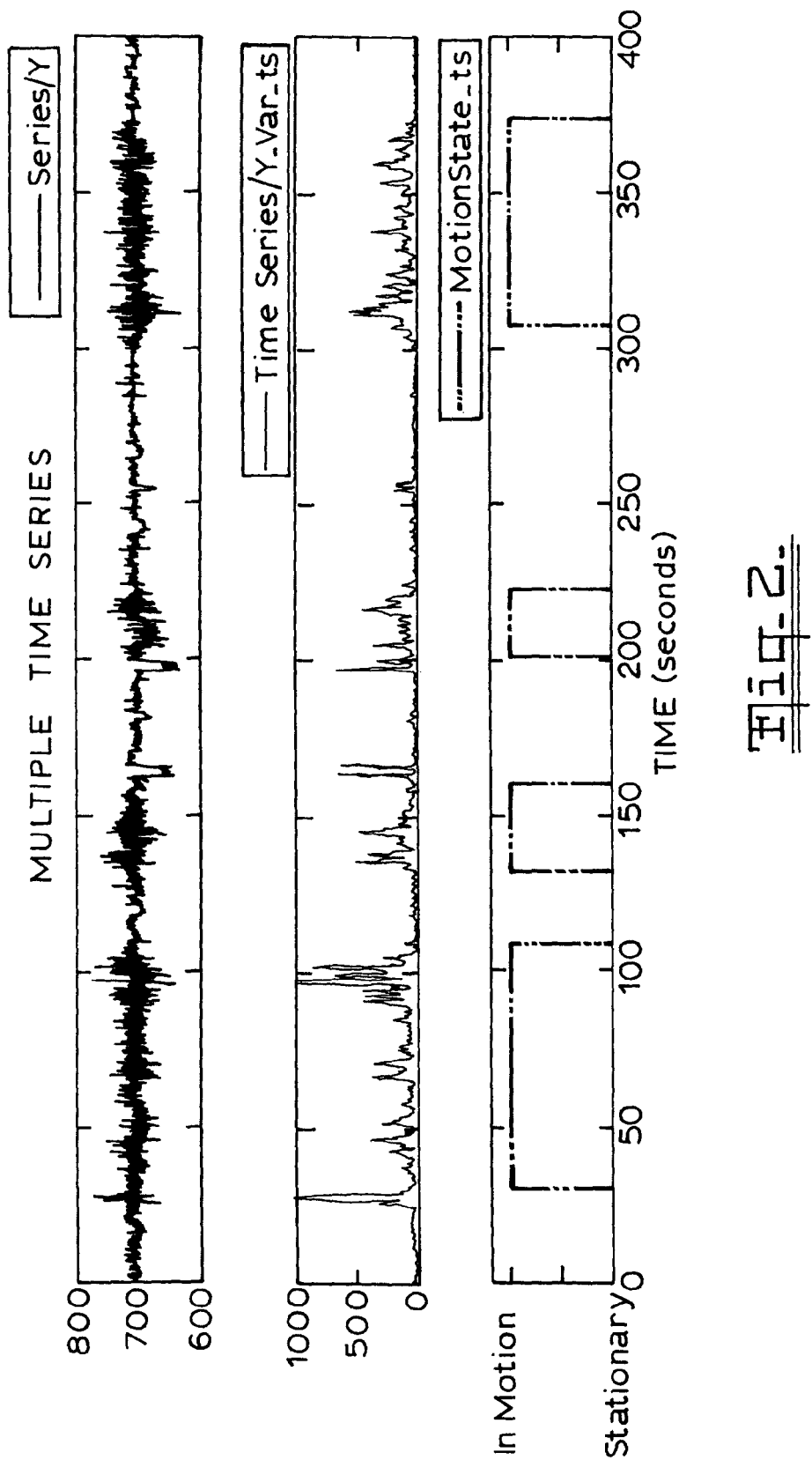
FIG. 2 illustrates data from the accelerometer showing (top) raw Y axis data, corresponding signal variance (middle) and motion state trace (lower) showing the two states of stationary and in motion.

FIG. 2 illustrates a graph of data recorded from a real driving session. Raw Y-axis data (blue) with corresponding signal variance (green). The Motion State trace shows the two vehicle states (Stationary & In Motion). It has been verified by video camera that the times of minimal signal variance correspond to when the vehicle is stationary.

From the above it can be seen that this invention provides a unique means of obtaining a measure of alertness and attention. The combination of head movements with eye movements enables a more accurate analysis of drowsiness states and the analysis of head movements either alone or combined with eye movement data enables the detection of many inattentive states Those skilled in the art will realise that this invention can be implemented in embodiments other than those described without departing from the core teachings of this invention.

The invention claimed is:

1. A head worn device for monitoring alertness and attention of a wearer which includes:
   a) sensors to monitor the wearer's eyelid and eye movements;
   b) a three-dimensional accelerometer to detect the wearer's head motion;
   c) data storage means for storing data from said sensors and said three-dimensional accelerometer;
   d) at least one microprocessor in communication with the data storage means to process the data from the sensors and the three-dimensional accelerometer to provide a measure of drowsiness and inattention;
   e) whereby the eyelid and eye movements are used to predict drowsiness and the head motion is used to detect inattention, and
   f) wherein the device is a pair of spectacles and the microprocessor analyzes the data from said three-dimensional accelerometer to determine if the vehicle is in motion.

2. An alertness and attention monitor for a vehicle driver, comprising:
   a) sensors to monitor eyelid and eye movements;
   b) a three-dimensional accelerometer to detect if the vehicle is in motion and whether the vehicle driver's head is tilted; wherein the three-dimensional accelerometer is coupled to a pair of spectacles;
   c) data storage means for storing data from said sensors and said three-dimensional accelerometer;
   d) at least one microprocessor in communication with the data storage means to process the data from the sensors and the three-dimensional accelerometer to provide a measure of drowsiness and inattention, and
   e) an alarm triggered in response to concurrent determinations by the microprocessor that (1) the vehicle driven by the vehicle driver is in motion; and (ii) a downward gaze of the vehicle driver has been sustained for a time period greater than a predetermined time period, and
   f) whereby the eyelid and eye movements are used to predict drowsiness and the detection of whether the vehicle driver's head is tilted is used to detect inattention.

3. The alertness and attention monitor for a vehicle of claim 2, wherein the spectacles have a frame and the three-dimensional accelerometer is in an arm of the spectacle frame.

* * * * *